US010534977B2

(12) United States Patent
Guo et al.

(10) Patent No.: US 10,534,977 B2
(45) Date of Patent: Jan. 14, 2020

(54) METHODS AND SYSTEMS FOR PERFORMING SEGMENTATION AND REGISTRATION OF IMAGES USING NEUTROSOPHIC SIMILARITY SCORES

(71) Applicants: H. LEE MOFFITT CANCER CENTER AND RESEARCH INSTITUTE, INC., Tampa, FL (US); Yanhui Guo, Miami, FL (US)

(72) Inventors: Yanhui Guo, Miami, FL (US); Segundo J. Gonzalez, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 16/214,520

(22) Filed: Dec. 10, 2018

(65) Prior Publication Data
US 2019/0251389 A1    Aug. 15, 2019

Related U.S. Application Data

(63) Continuation of application No. 15/121,246, filed as application No. PCT/US2015/017362 on Feb. 24, 2015, now Pat. No. 10,152,796.
(Continued)

(51) Int. Cl.
G06K 9/62        (2006.01)
G06T 7/30        (2017.01)
(Continued)

(52) U.S. Cl.
CPC ............ *G06K 9/6202* (2013.01); *A61B 90/37* (2016.02); *G02B 27/0172* (2013.01);
(Continued)

(58) Field of Classification Search
CPC .............. A61B 90/37; A61B 2090/365; A61B 2090/502; A61B 2576/00; G02B 27/0172;
(Continued)

(56) References Cited

U.S. PATENT DOCUMENTS 6,647,142 B1   11/2003  Beardsley
7,478,091 B2    1/2009  Mojsilovic et al.
(Continued)

OTHER PUBLICATIONS

PCT/US2015/017362, International Search Report and Written Opinion, dated Jun. 3, 2015.
(Continued)

*Primary Examiner* — Edward Park
(74) *Attorney, Agent, or Firm* — Meunier Carlin & Curfman LLC

(57) ABSTRACT

An example method for segmenting an object contained in an image includes receiving an image including a plurality of pixels, transforming a plurality of characteristics of a pixel into respective neutrosophic set domains, calculating a neutrosophic similarity score for the pixel based on the respective neutrosophic set domains for the characteristics of the pixel, segmenting an object from background of the image using a region growing algorithm based on the neutrosophic similarity score for the pixel, and receiving a margin adjustment related to the object segmented from the background of the image.

19 Claims, 9 Drawing Sheets

Related U.S. Application Data

(60) Provisional application No. 61/943,622, filed on Feb. 24, 2014.

(51) Int. Cl.

| | | |
|---|---|---|
| *G06T 7/11* | (2017.01) | |
| *G06T 7/187* | (2017.01) | |
| *A61B 90/00* | (2016.01) | |
| *G02B 27/01* | (2006.01) | |
| *G06T 11/60* | (2006.01) | |
| *A61B 90/50* | (2016.01) | |

(52) U.S. Cl.
CPC ............. *G06K 9/6215* (2013.01); *G06T 7/11* (2017.01); *G06T 7/187* (2017.01); *G06T 7/30* (2017.01); *G06T 11/60* (2013.01); *A61B 2090/365* (2016.02); *A61B 2090/502* (2016.02); *A61B 2576/00* (2013.01); *G02B 2027/0141* (2013.01); *G06T 2207/10136* (2013.01); *G06T 2207/30004* (2013.01)

(58) Field of Classification Search
CPC ......... G02B 2027/0141; G06K 9/6202; G06K 9/6215; G06T 11/60; G06T 7/0081; G06T 7/11; G06T 7/187; G06T 7/30; G06T 2207/10136; G06T 2207/30004
See application file for complete search history.

(56) References Cited

U.S. PATENT DOCUMENTS

| | | | | |
|---|---|---|---|---|
| 9,443,161 | B2 | 9/2016 | Guo | |
| 10,152,796 | B2* | 12/2018 | Guo | G06K 9/6202 |
| 2003/0026588 | A1* | 2/2003 | Elder | G08B 13/19643 |
| | | | | 386/230 |
| 2006/0002615 | A1* | 1/2006 | Fu | A61B 6/5235 |
| | | | | 382/254 |
| 2006/0002631 | A1* | 1/2006 | Fu | G06K 9/3233 |
| | | | | 382/294 |
| 2006/0274928 | A1 | 12/2006 | Collins et al. | |
| 2008/0292194 | A1* | 11/2008 | Schmidt | G06T 7/0012 |
| | | | | 382/217 |
| 2011/0072397 | A1* | 3/2011 | Baker | G06T 19/00 |
| | | | | 715/852 |
| 2011/0160578 | A1* | 6/2011 | Tripathi | A61B 90/37 |
| | | | | 600/427 |
| 2013/0208966 | A1* | 8/2013 | Zhao | G06F 9/5072 |
| | | | | 382/131 |
| 2016/0180195 | A1* | 6/2016 | Martinson | G06K 9/6256 |
| | | | | 382/103 |
| 2016/0364878 | A1* | 12/2016 | Guo | G06K 9/6202 |

OTHER PUBLICATIONS

Shan et al., "A Completely Automatic Segmentation Method for Breast Ultrasound Images Using Region Growing," Dec. 2008, retrieved from Internet on Apr. 30, 2015, <URL:http://www.google.com/url?sa=t&rct=j&q=&esrc=s&source=web&cd=1 &cad=~a &uact=8&ved=OCCEQFjAA&url=http%3A%2F%2Fwww.atlantis-press.com%2Fphp%2Fdownload_paper.php%3Fid%3D1722&ei=OWtCVYbDJaIlsATujIGQCg&usg=AFQjCNGttM3s71BrIIUY14iApNBLor64wQ&sig2=oKOwYStKoVyCXdo.

Sengur et al., "Color Texture Image Segmentation based on Neutrosophic Set and Wavelet Transformation," Computer Vision and Image Understanding. vol. 115 2011. pp. 1134-1144, [retrieved on Apr. 17, 2015]. Retrieved from the Internet: <URL:http://www.researchgate.net/profile/Abdulkadir_Sengur/publication/220134488_Color_texture_image_segmentation_based_on_neutrosophic_set_and_wavelet_transformation/links/544deba9.

Guo et al., "A New Neutrosophic Approach to Image Thresholding," Proceedings of the 11th Joint Conference on Information Science, 2008.

Yang et al., "Automatic 3D Segmentation of Ultrasound Images Using Atlas Registration and Statistical Texture Prior," Proc SPIE, 2011.

Zhang, Ming, "Novel Approaches to Image Segmentation Based on Neutrosophic Logic," Digital Commons @ Utah State University, 2010.

Buddingh, et al., "Intraoperative assessment of biliary anatomy for prevention of bile duct injury: a review of current and future patient safety interventions", Surg Endosc. 2011;25:2449-2461.

Cannon, et al., "Real-time three-dimensional ultrasound for guiding surgical tasks", Comput Aided Surg. 2003;8:82-90.

Gao, et al., "Prostate segmentation by sparse representation based classification", Med Image Comput Comput Assist Interv. 2012;15:451-458.

Horsch, et al., "Automatic segmentation of breast lesions on ultrasound", Med. Phys. 2001;28(8):1652-1659.

Keereweer, et al., "Optical image-guided surgery—Where do we stand?", Mol Imaging Biol. 2011;13:199-207.

Liu, et al., "Fully automatic 3D segmentation of iceball for image-guided cryoablation", Conf Proc IEEE Eng Med Biol Soc. 2012;2012:2327-2330.

Nakano, et al., "Fusion of MRI and sonography image for breast cancer evaluation using real-time virtual sonography with magnetic navigation: first experience", Jpn J Clin Oncol. 2009;39(9):552-559.

Risholm, et al., "Multi-modal image registration for pre-operative planning and image guided neurosurgical procedures", Neurosurg Clin N Am. 2011; 22(2): 197-206.

\* cited by examiner

Table 1. Single Tumor Phantoms. Accuracy of detection per axis, and overall volume accuracy

|  | X (mm) | Y (mm) | Z (mm) | Δ Volume (mm³) |
|---|---|---|---|---|
| Ave Δ | 0.95 | 1.38 | 0.85 | 1.11 |
| SD | 1.38 | 1.21 | 0.95 | 1.82 |
| SEM | 0.40 | 0.35 | 0.27 | 0.039 |

Table 2. Human Breast Tumors. Accuracy of detection per axis, and overall volume accuracy.

|  | X (mm) | Y (mm) | Z (mm) | Δ Volume (mm³) |
|---|---|---|---|---|
| Ave Δ | 7.62 | 3.81 | 1.27 | 36.87 |
| SD | 3.592102 | 2.743514 | 1.036951 | 10.21 |
| SEM | 2.073901 | 1.583968 | 0.598684 | 1.96 |

METHODS AND SYSTEMS FOR PERFORMING SEGMENTATION AND REGISTRATION OF IMAGES USING NEUTROSOPHIC SIMILARITY SCORES

CROSS-REFERENCE TO RELATED APPLICATIONS

This application is a continuation of U.S. patent application Ser. No. 15/121,246, filed on Aug. 24, 2016, entitled "METHODS AND SYSTEMS FOR PERFORMING SEGMENTATION AND REGISTRATION OF IMAGES USING NEUTROSOPHIC SIMILARITY SCORES," which is national stage application filed under 35 U.S.C § 371 of PCT/US2015/017362, filed on Feb. 24, 2015, which claims the benefit of U.S. Provisional Patent Application No. 61/943,622, filed on Feb. 24, 2014, entitled "METHODS AND SYSTEMS FOR PERFORMING SEGMENTATION AND REGISTRATION OF IMAGES USING NEUTROSOPHIC SIMILARITY SCORES," the disclosures of which are expressly incorporated herein by reference in their entireties.

BACKGROUND

Real-time visualization is an actively growing area in different scientific areas. The medical field is not an exception, and tumors, vessels and organs are visualized more accurately as technology improves, and recently the potential to perform a real-time visualization has not only been possible but the addition of this technology have shown improved results in interventional procedures. Buddingh K T, et al. "Intraoperative assessment of biliary anatomy for prevention of bile duct injury: a review of current and future patient safety interventions." *Surg Endosc.* 2011; 25:2449-61; Keereweer S, et al. "Optical image-guided surgery—where do we stand?" Mol Imaging Biol. 2011; 13:199-207; and Cannon J W, Stoll J A, et al. "Real-time three-dimensional ultrasound for guiding surgical tasks." *Comput Aided Surg.* 2003; 8:82-90. Furthermore, during a real-time visualization and evaluation, prior analysis of a particular area or volume of interest could be imported, to assist in the current evaluation of the image. Nakano S, et al. "Fusion of MRI and sonography image for breast cancer evaluation using real-time virtual sonography with magnetic navigation: first experience." *Jpn J Clin Oncol.* 2009; 39:552-9. Conventional techniques involve co-registration and segmentations algorithms.

Co-registration techniques display prior images, with their associated analysis, and import them as the real-time image, approximating its position and orientation based on software calculation. This position is approximated using different methods such as marking the patient (tattooing), placing the patient on the table in a very similar position as in the prior exam, or using real-time imaging (e.g., ultrasound co-registration) to approximate the area where the data should be imported. Regardless of the co-registration technique, this image is not the "real-time" image and any changes is position, manipulation of surrounding tissues or simple changes in tissue volumes (secondary to the pliability of the tissues) render this static, prior image inaccurate. Segmentation techniques are similarly powerful and allow the user to visualize a particular organ or area of interest in a user friendly fashion. These techniques recognize particular tissues based on their image intensities and can show them in a three-dimensional manner and some of them in an automatic fashion. Gao Y, et al. "Prostate segmentation by sparse representation based classification." *Med Image Comput Comput Assist Interv.* 2012; 15:451-8; Liu X, et al. "Fully automatic 3D segmentation of iceball for image-guided cryoablation." *Conf Proc IEEE Eng Med Biol Soc.* 2012; 2012:2327-30. The drawback of these techniques is the limited ability to import prior analysis, preventing useful prior evaluations to be considered during this real-time assessment.

SUMMARY

Techniques for providing real-time visualization are described herein that are capable of importing a prior analysis of a specific data onto real-time images such as real-time, intra-operative images. A region growing algorithm for performing an image segmentation based on neutrosophic similarity scores is described. This region growing algorithm can be applied to extract an object (e.g., a lesion region of interest such as a tumor, organ or other tissue of interest) from a pre-operative image (e.g., the "first image" as also described herein). As used herein, a pre-operative image is scanned, and optionally analyzed, before a medical procedure. For example, the pre-operative image can be an image of a breast tumor. Following segmentation, a medical professional (e.g., a radiologist) can analyze and annotate the pre-operative image and/or the object extracted there from, and this analysis can be stored for subsequent use. During the surgery, a real-time, intra-operative image (e.g., the "second image" as also described herein) can be captured. A registration algorithm for registering the pre-operative image and the real-time, intra-operative based on neutrosophic similarity scores is described. According to the registration algorithm, the segmentation results in the pre-operative image can be used as reference. Following registration, the prior analysis, which is stored for subsequent use, can be overlaid (e.g., after being coordinated and adjusted) on the real-time, intra-operative image. Accordingly, the prior analysis can be imported onto or fused with the real-time, intra-operative medical image, which can be used by a medical professional (e.g., a surgeon) during the surgery for guidance. This allows the surgeon to see the real-time area of interest, without the need of importing static, less accurate images. In other words, this allows the surgeon to visualize the area of interest in real-time, which can improve surgical resections.

An example method for segmenting an object contained in an image includes receiving an image including a plurality of pixels, transforming a plurality of characteristics of a pixel into respective neutrosophic set domains, calculating a neutrosophic similarity score for the pixel based on the respective neutrosophic set domains for the characteristics of the pixel, segmenting an object from background of the image using a region growing algorithm based on the neutrosophic similarity score for the pixel, and receiving a margin adjustment related to the object segmented from the background of the image. The steps for segmenting can be performed using at least one processor. Optionally, the processor can be part of a cloud computing environment.

The image can provide a two-dimensional ("2D") or three-dimensional ("3D") visualization of the object, for example. Example imaging modalities that provide 2D or 3D visualizations include, but are not limited to, ultrasound imaging, photoacoustic imaging, magnetic resonance imaging ("MRI"), computed tomography ("CT") imaging, fluoroscopic imaging, x-ray imaging, fluorescence imaging and nuclear scan imaging. In addition, the object can be a lesion region of interest such as a tumor, organ or other tissue of interest, for example.

Additionally, the method can include receiving an annotation related to the object segmented from the background of the image. For example, a medical professional such as a radiologist can analyze the image and/or the object and provide the annotation (e.g., measurements, labels, notes, etc.) in order to highlight features (e.g., suspicious areas, blood vessels, vital structures, surrounding organs, etc.) contained within the image and/or the object. It should be understood that the annotations can be used by another medical professional such as a surgeon, for example, as guidance during a subsequent medical procedure or consultation. Additionally, the method can further include storing the annotation related to the object segmented from the background of the image. As described below, the annotation related to the object segmented from the image can be overlaid on a real-time, image such as an intra-operative image.

Additionally, when using the region growing algorithm, the pixel can be merged into a region containing the object under the condition that the neutrosophic similarity score for the pixel is less than a threshold value, and the pixel can be merged into a region containing the background under the condition that the neutrosophic similarity score for the pixel is greater than a threshold value.

Alternatively or additionally, the plurality of characteristics can include an intensity of the pixel, a textural value of the pixel and/or a homogeneity of the pixel. Additionally, the step of calculating the neutrosophic similarity score for the pixel based on the respective neutrosophic set domains for the characteristics of the pixel can include calculating respective neutrosophic similarity scores for each of the respective neutrosophic set domains, and calculating a mean of the respective neutrosophic similarity scores for each of the respective neutrosophic set domains. In addition, the intensity of the pixel can be transformed into an intensity neutrosophic set domain based on an intensity value. Alternatively or additionally, the homogeneity of the pixel can be transformed into a homogeneity neutrosophic set domain based on a homogeneity value. The method can further include filtering the image to obtain the homogeneity of the pixel.

Alternatively or additionally, each of the respective neutrosophic set domains can include a true value, an indeterminate value and a false value.

An example method for registering a plurality of images containing an object can include receiving a first image including a plurality of pixels, calculating respective first neutrosophic similarity scores for each of the pixels of the first image, segmenting an object from background of the first image using a region growing algorithm based on the respective first neutrosophic similarity scores for each of the pixels, and receiving a margin adjustment related to the object segmented from the background of the image. The method can also include receiving a second image including a plurality of pixels, and calculating respective second neutrosophic similarity scores for each of the pixels of the second image. The method can further include performing a template matching algorithm based on differences between the respective first and second neutrosophic similarity scores for each of the pixels of the first and second images, respectively, to determine one or more registration parameters, and registering the first and second images using the one or more registration parameters. The steps for registering the plurality of images can be performed using at least one processor. Optionally, the processor can be part of a cloud computing environment.

The first and second images can provide a 2D or 3D visualization of the object, for example. Example imaging modalities that provide 2D or 3D visualizations include, but are not limited to, ultrasound imaging, photoacoustic imaging, MRI, CT imaging, fluoroscopic imaging, x-ray imaging, fluorescence imaging and nuclear scan imaging. In addition, the object can be a lesion region of interest such as a tumor, organ or other tissue of interest, for example.

Additionally, the registration parameters can be determined by minimizing the differences between the respective first and second neutrosophic similarity scores for each of the pixels of the first and second images, respectively.

Alternatively or additionally, the method can further include segmenting the object from background in the second image using the region growing algorithm based on the respective second neutrosophic similarity scores for each of the pixels. Alternatively or additionally, the method can further include receiving a margin adjustment related to the object segmented from the background of the second image.

Additionally, when using the region growing algorithm, the pixel can be merged into a region containing the object under the condition that the neutrosophic similarity score for the pixel is less than a threshold value, and the pixel can be merged into a region containing the background under the condition that the neutrosophic similarity score for the pixel is greater than a threshold value.

Alternatively or additionally, the step of calculating the respective first or second neutrosophic similarity scores for each of the pixels of the first or second image can include transforming a plurality of characteristics of each of the pixels of the first or second image into respective neutrosophic set domains, and calculating the respective first or second neutrosophic similarity scores for each of the pixels based on the respective neutrosophic set domains for the characteristics of each of the pixels.

Alternatively or additionally, the plurality of characteristics can include a respective intensity of each of the pixels, a respective textural value of each of the pixels and/or a respective homogeneity of each of the pixels. Additionally, the step of calculating the respective first or second neutrosophic similarity scores for each of the pixels based on the respective neutrosophic set domains for the characteristics of each of the pixels can include calculating respective neutrosophic similarity scores for each of the respective neutrosophic set domains, and calculating a mean of the respective neutrosophic similarity scores for each of the respective neutrosophic set domains. In addition, the respective intensity of each of the pixels can be transformed into an intensity neutrosophic set domain based on a respective intensity value. Alternatively or additionally, the respective homogeneity of each of the pixels can be transformed into a homogeneity neutrosophic set domain based on a respective homogeneity value. The method can further include filtering the image to obtain the respective homogeneity of the pixel.

Alternatively or additionally, each of the respective neutrosophic set domains can include a true value, an indeterminate value and a false value.

Alternatively or additionally, the method can further include receiving an annotation related to the object segmented from the background of the first image. For example, a medical professional such as a radiologist can analyze the image and/or the object and provide the annotation measurements, labels, notes, etc.) in order to highlight features (e.g., suspicious areas, blood vessels, vital structures, surrounding organs, etc.) contained within the first image and/or the object. It should be understood that the annotations can be used by another medical professional such as a surgeon, for example, as guidance during a subsequent medical procedure or consultation. Additionally, the method can further include storing the annotation related to the object segmented from the background of the image. Optionally, the method can further include overlaying the annotation relative to the object segmented from the background of the second image.

Alternatively or additionally, the method can further include transmitting the second image with the overlaid annotation to an augmented reality ("AR") head-mounted device, and displaying the second image with the overlaid annotation on the AR head-mounted device. Optionally, the method can further include receiving information regarding a user's movement from the AR head-mounted device, adjusting a position and/or an orientation of the second image with the overlaid annotation, and transmitting the adjusted second image with the overlaid annotation to the AR head-mounted device, for example, for display on the AR head-mounted device.

Additionally, the first image can be a pre-operative image. The pre-operative image can be the image that is analyzed by the medical professional (e.g., a radiologist) and annotated as described above. In addition, the second image can be a real-time, intra-operative image. The real-time, intra-operative image can have the annotation from the pre-operative image overlaid thereon, which can aid the other medical professional (e.g., a surgeon) during a subsequent medical procedure or consultation.

It should be understood that the above-described subject matter may also be implemented as a computer-controlled apparatus, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 5 are tables showing the results of a feasibility study for the region growing and segmentation algorithms described herein.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for performing image segmentation and registration algorithms on medical images (e.g., ultrasound images) based on neutrosophic similarity scores, it will become evident to those skilled in the art that the implementations are not limited thereto, but are applicable for performing image segmentation and registration algorithms on other types of images including, but not limited to, photoacoustic images, MRIs, CT images, fluoroscopic images, x-ray images, fluorescence images and nuclear scan images. The image segmentation and registration algorithms can be used to provide real-time, 3D visualization of tumors in soft tissue (e.g., breast tumors, melanoma, etc.), which facilitates bedside procedures to assess tumor response and/or place central lines. The image segmentation and registration algorithms can also be used to provide real-time, 3D visualization during surgical procedures, for example, for guidance during laparoscopic and robotic surgeries of deep abdominal organs or for guidance during vascular procedures. It will also become evident that the segmentation and registration algorithms are applicable to fields other than medicine.

Figure 1:
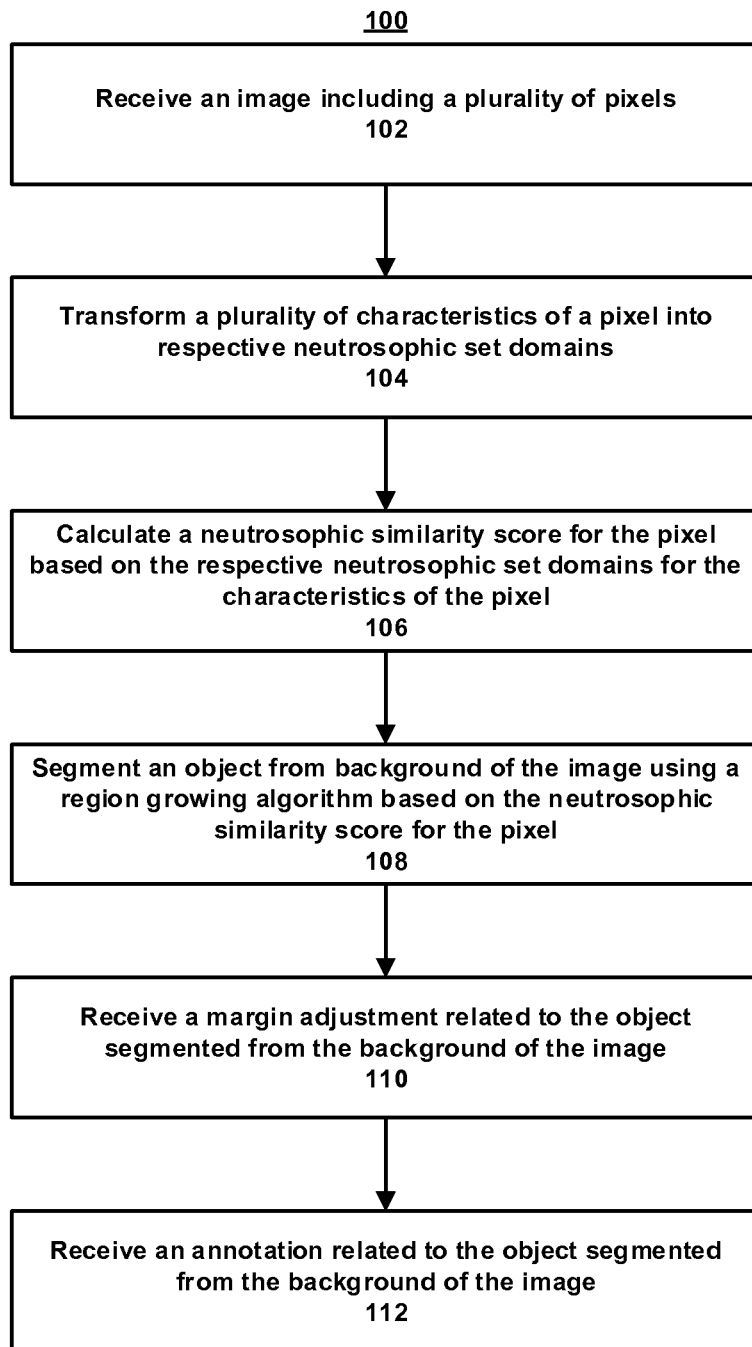
FIG. 1 is a flow diagram illustrating example operations for performing a region growing algorithm based on neutrosophic similarity scores.
Figure 2:
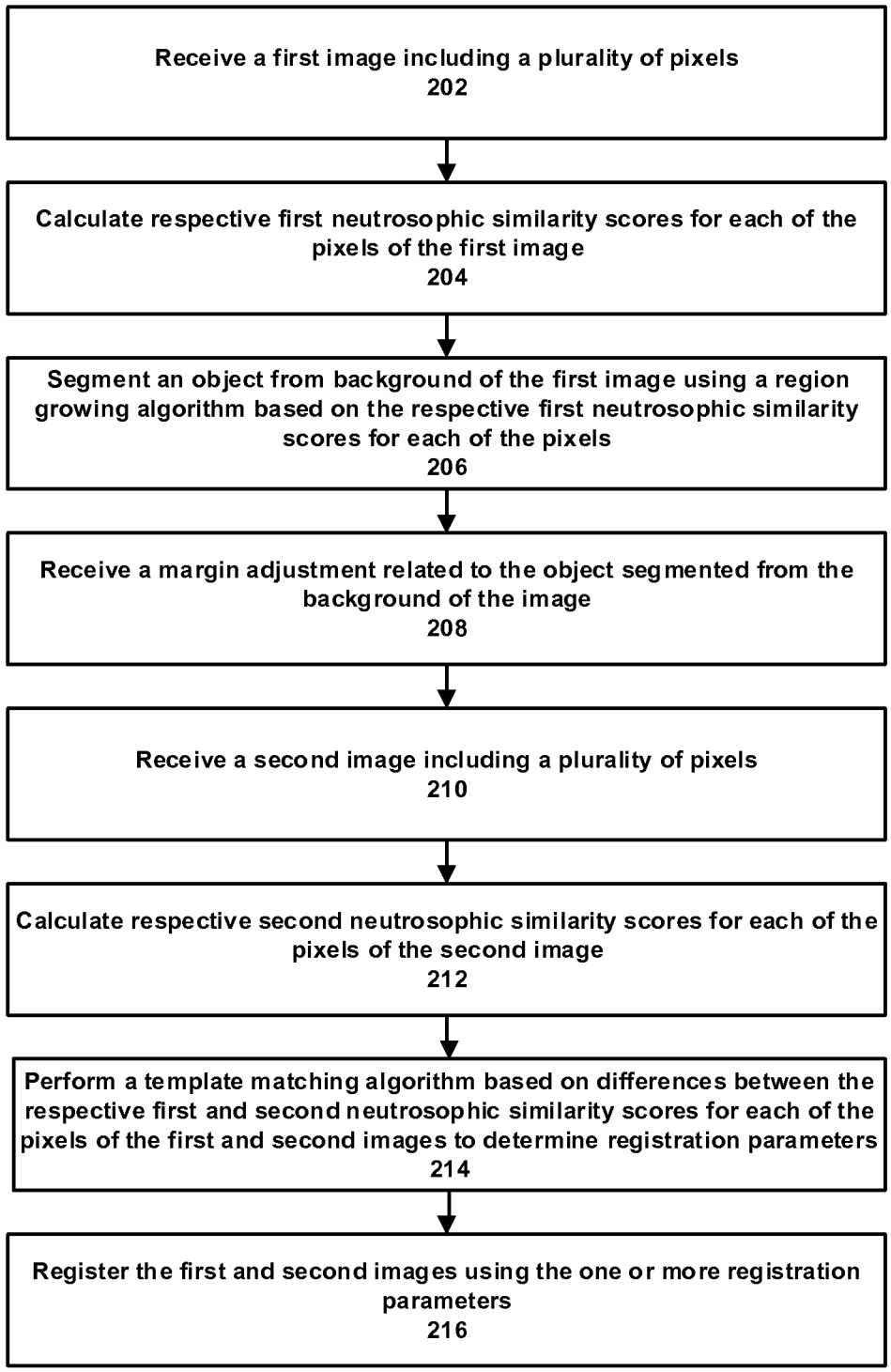
FIG. 2 is a flow diagram illustrating example operations for performing image registration based on neutrosophic similarity scores.

Referring now to FIGS. 1 and 2, example image segmentation and registration techniques are described. It should be understood that the image segmentation and registration techniques can be performed by at least one processor (described below). Additionally, the image segmentation and registration techniques can optionally be implemented within a cloud computing environment, for example, in order to decrease the time needed to perform the algorithms, which can facilitate visualization of the prior analysis on real-time images. Cloud computing is well-known in the art. Cloud computing enables network access to a shared pool of configurable computing resources (e.g., networks, servers, storage, applications, and services) that can be provisioned and released with minimal interaction. It promotes high availability, on-demand self-services, broad network access, resource pooling and rapid elasticity. It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring now to FIG. 1, a flow diagram illustrating example operations 100 for performing a region growing algorithm based on neutrosophic similarity scores is shown. At 102, an image including a plurality of pixels is received. The image can provide a 2D or 3D visualization of an object, for example. Example imaging modalities that provide 2D or 3D visualizations include, but are not limited to, ultrasound imaging, photoacoustic imaging, MRI, CT imaging, fluoroscopic imaging, x-ray imaging, fluorescence imaging and nuclear scan imaging. In the examples provided below, the image is a 3D ultrasound image, for example, acquired with by the iU22 xMATRIX ULTRASOUND SYSTEM from KONINKLIJKE PHILIPS N.V. of EINDHOVEN, THE NETHERLANDS. 3D ultrasound systems are portable, relatively inexpensive, and do not subject a patient to ionizing radiation, which provide advantages over CT scans (radiation exposure) and MRIs (relatively large system) for real-time image guidance. However, as described above, this disclosure contemplates using images acquired by any imaging modality that provides a 2D or 3D visualization. Additionally, the object can be a lesion region of interest such as a tumor, organ or other tissue of interest, for example. In the examples provided below, the image is an image of breast tissue of a subject and the object is a tumor. However, as described above, this disclosure contemplates using images of other tissue and objects other than tumors. The subject or patient described herein can be human and non-human mammals of any age.

At 104, a plurality of characteristics of a pixel are transformed into respective neutrosophic set domains. Each of the respective neutrosophic set domains can include a true value, an indeterminate value and a false value. Additionally, the plurality of characteristics can include, but are not limited to, an intensity value of the pixel, a textural value of the pixel and/or a homogeneity value of the pixel. In other words, this disclosure contemplates transforming pixel characteristics other than intensity, texture and homogeneity into neutrosophic set domains. In the examples described below, an intensity image and a homogeneity image are transformed into respective neutrosophic set domains. Although the examples involve transforming two pixel characteristics into respective neutrosophic set domains and calculating a neutrosophic similarity score there from, this disclosure contemplates transforming more or less than two pixel characteristics (e.g., one, three, four, etc. pixel characteristics) into respective neutrosophic set domains and calculating a neutrosophic similarity score there from.

The intensity image can be defined using intensity values for the pixels and transformed into the neutrosophic set domain as shown by Eqns. (1)-(5).

$$T_{In}(i, j) = \frac{g(i, j) - g_{min}}{g_{max} - g_{min}} \quad (1)$$

$$I_{In}(i, j) = \frac{\delta(i, j) - \delta_{min}}{\delta_{max} - \delta_{min}} \quad (2)$$

$$\delta(i, j) = \text{abs}(g(i, j) - \bar{g}(i, j)) \quad (3)$$

$$\bar{g}(i, j) = \frac{1}{w \times w} \sum_{m=i-w/2}^{i+w/2} \sum_{n=j-w/2}^{j+w/2} g(m, n) \quad (4)$$

$$F_{In}(i, j) = 1 - T(i, j) \quad (5)$$

where $\bar{g}(i, j)$ is the local mean value, and $\delta(i, j)$ is the absolute value of the difference between intensity $g(i, j)$ and its local mean value at $(i, j)$, and i and j are pixel coordinates in the intensity image.

The homogeneity image can be defined using texture values for the pixels and transformed into neutrosophic set domain as shown by Eqns. (6)-(9). To obtain the homogeneity image (e.g., homogeneity values for each of the pixels), the image can be filtered, for example, using a texture energy measurement ("TEM") filter, mean filter, Gaussian filter, median filter, etc.

$$T_{Ho}(x, y) = \frac{H(x, y) - H_{min}}{H_{max} - H_{min}} \quad (6)$$

$$I_{Ho}(x, y) = 1 - \frac{Gd_h(i, j) - Gd_{h\ min}}{Gd_{h\ max} - Gd_{h\ min}} \quad (7)$$

$$F_{Ho}(x, y) = 1 - T_{Ho}(x, y) \quad (8)$$

$$H(x, y) = TEM(g(x, y)) \quad (9)$$

where $H(x, y)$ is the homogeneity value at $(x, y)$, which is depicted as the filtering result with the TEM filters. $Gd_h(x, y)$ is the gradient magnitude on $H(x, y)$, x and y are pixel coordinates in the homogeneity image.

At 106, a neutrosophic similarity score for the pixel can be calculated based on the respective neutrosophic set domains for the characteristics of the pixel. For example, respective neutrosophic similarity scores for each of the respective neutrosophic set domains (e.g., the neutrosophic set domains for the intensity values and the homogeneity values) can be calculated as shown by Eqns. (10)-(11). The neutrosophic similarity score for the intensity image ($NS_{In}(x, y)$) is shown by Eqn. (10), and the neutrosophic similarity score for the homogeneity image ($NS_{Ho}(x, y)$) is shown by Eqn. (11).

$$NS_{In}(x, y) = \frac{T_{In}(x, y)}{\sqrt{T_{In}^2(x, y) + I_{In}^2(x, y) + F_{In}^2(x, y)}} \quad (10)$$

$$NS_{Ho}(x, y) = \frac{T_{Ho}(x, y)}{\sqrt{T_{Ho}^2(x, y) + I_{Ho}^2(x, y) + F_{Ho}^2(x, y)}} \quad (11)$$

Then, a mean of the respective neutrosophic similarity scores for each of the respective neutrosophic set domains (e.g., the neutrosophic set domains for the intensity values and the homogeneity values) can be calculated as shown by Eqn. (12). As described above, a mean of any number of neutrosophic similarity scores (e.g., one for each pixel characteristic transformed into the neutrosophic set domain) can be calculated.

$$NS = \frac{NS_{In} + NS_{Ho}}{2} \quad (12)$$

At 108, an object (e.g., a lesion region of interest such as a tumor, organ or other tissue of interest) can be segmented from background of the image using a region growing algorithm based on the neutrosophic similarity score for the pixel. For example, an initial region or seed points can be selected on the image, and neighboring pixels (e.g., pixels neighboring or adjacent to the initial region or seed points) can grow into the object region according their respective neutrosophic similarity score differences ($\text{Dif}_{NS}$), which is shown by Eqn. (13). If the difference is less than a threshold value, a pixel can be merged into the object region. If the difference is greater than the threshold value, a pixel can be merged into the background region. This step (e.g., step 108) is iteratively performed until no pixels satisfies the criterion.

$$\text{Dif}_{NS} = NS(i,j) - \overline{\text{Obj}_{NS}} \quad (13)$$

where $NS(i,j)$ is the neutrosophic similarity score at pixel, $\text{Obj}_{NS}$ is a neutrosophic similarity score for the object region and i and j are pixel coordinates.

At 110, a margin adjustment related to the object segmented from the background of the image can be received. The margin adjustment is an adjustment to the margins or boundaries around the object segmented from the background of the image. For example, a medical professional (e.g., a radiologist) can review the segmented image, and based on his knowledge and experience, manually refine (e.g., expand or contract) the margins or boundaries of the object segmented using the region growing algorithm. This disclosure contemplates that the segmented object can be displayed in a 2D or 3D rendering with or without performing the margin adjustment. Optionally, the segmented object can be displayed using an AR head-mounted device (described below).

Optionally, at 112, an annotation related to the object segmented from the background of the image can be received. For example, a medical professional (e.g., a radiologist) can analyze the segmented image and/or the object and provide the annotation (measurements, labels, notes, etc.) in order to highlight features (e.g., suspicious areas, blood vessels, vital structures, surrounding organs, etc.) contained within the image and/or the object. It should be understood that the annotations can be used by another medical professional such as a surgeon, for example, as guidance during a subsequent medical procedure or consultation. The annotation is also referred to herein as the "prior analysis." The annotation related to the object segmented from the background of the image can be stored, for example, for subsequent use by overlaying and displaying the annotation relative to a real-time, intra-operative image (described below). This disclosure contemplates that the segmented object and/or the annotation can be displayed in a 2D or 3D rendering with or without performing the margin adjustment. Optionally, the segmented object and/or the annotation can be displayed using an AR head-mounted device (described below).

Referring now to FIG. 2, a flow diagram illustrating example operations for performing image registration based on neutrosophic similarity scores is shown. At 202, a first image including a plurality of pixels can be received. Similar as above, the first image can provide a 2D or 3D visualization of the object, for example. Optionally, the first image can be a pre-operative image providing a 2D or 3D visualization of the object. The first image can be segmented and optionally analyzed to provide guidance to a medical professional (e.g., a surgeon) during a medical procedure (e.g., surgery). Accordingly, the first image can also be referred to as the "analyzed image." Additionally, the object can be a lesion region of interest such as a tumor, organ or other tissue of interest, for example. In the examples provided below, the image is an image of breast tissue of a subject and the object is a tumor.

At 204, respective first neutrosophic similarity scores for each of the pixels of the first image can be calculated. Neutrosophic similarity scores for the pixels of the first image can be calculated as described above. For example, a single pixel characteristic can be transformed into the neutrosophic set domain. Optionally, a plurality of pixel characteristics can be transformed into the neutrosophic set domain. The neutrosophic set domain can include a true value, an indeterminate value and a false value. Transforming a pixel characteristic into the neutrosophic set domain is shown by Eqns. (1)-(5) for intensity values and Eqns. (6)-(9) for homogeneity values. The pixel characteristics can include, but are not limited to, an intensity of the pixel, a textural value of the pixel and/or a homogeneity of the pixel. Additionally, neutrosophic similarity scores can be calculated, for example, as shown by Eqn. (10) for intensity values and Eqn. (11) for homogeneity values. Optionally, when neutrosophic scores for a plurality of pixel characteristics are calculated, a mean of the neutrosophic similarity scores can be calculated as shown by Eqn. (12).

At 206, an object can be segmented from background of the first image using a region growing algorithm based on the respective first neutrosophic similarity scores for each of the pixels. As described above, an initial region or seed points can be selected on the first image, and neighboring pixels (e.g., pixels neighboring or adjacent to the initial region or seed points) can grow into the object region according their respective neutrosophic similarity score differences ($\text{Dif}_{NS}$), which is shown by Eqn. (13). If the difference is less than a threshold value, a pixel can be merged into the object region. If the difference is greater than the threshold value, a pixel can be merged into the background region. This step (e.g., step 206) is iteratively performed until no pixels satisfies the criterion. At 208, a margin adjustment related to the object segmented from the background of the image can be received. As described above, the margin adjustment is an adjustment to the margins or boundaries around the object segmented from the background of the first image. For example, a medical professional (e.g., a radiologist) can review the segmented image, and based on his knowledge and experience, manually refine (e.g., expand or contract) the margins or boundaries of the object segmented using the region growing algorithm.

At 210, a second image including a plurality of pixels can be received. Similar as above, the second image can provide a 2D or 3D visualization of the object, for example. Optionally, the second image can be a real-time, intra-operative image providing a 2D or 3D visualization of the object. The second image can optionally be acquired with a 3D ultrasound system, which is portable, relatively inexpensive, and does not subject a patient to ionizing radiation, and therefore, makes it desirable for use in image guided surgery. Additionally, the object can be a lesion region of interest such as a tumor, organ or other tissue of interest, for example. In the examples provided below, the image is an image of breast tissue of a subject and the object is a tumor. The object in the second image (e.g., the real-time, intraoperative image) can be the same object (e.g., the same breast tumor) as the object in the first image (e.g., the pre-operative image).

At 212, respective second neutrosophic similarity scores for each of the pixels of the second image can be calculated. Neutrosophic similarity scores for the pixels of the second image can be calculated as described above. For example, a single pixel characteristic can be transformed into the neutrosophic set domain. Optionally, a plurality of pixel characteristics can be transformed into the neutrosophic set domain. The neutrosophic set domain can include a true value, an indeterminate value and a false value. Transforming a pixel characteristic into the neutrosophic set domain is shown by Eqns. (1)-(5) for intensity values and Eqns. (6)-(9) for homogeneity values. The pixel characteristics can include, but are not limited to, an intensity of the pixel, a textural value of the pixel and/or a homogeneity of the pixel. Additionally, neutrosophic similarity scores can be calculated, for example, as shown by Eqn. (10) for intensity values and Eqn. (11) for homogeneity values. Optionally, when neutrosophic scores for a plurality of pixel characteristics are calculated, a mean of the neutrosophic similarity scores can be calculated as shown by Eqn. (12). The respective second neutrosophic similarity scores for each of the pixels of the second image (e.g., the real-time, intra-operative image) can be based on the same pixel characteristic(s) as the respective first neutrosophic similarity scores for each of the pixels of the first image (e.g., the pre-operative image).

At 214, a template matching algorithm can be performed based on differences between the respective first and second neutrosophic similarity scores for each of the pixels of the first and second images, respectively, to determine one or more registration parameters. The registration parameters can be determined by minimizing the differences between the respective first and second neutrosophic similarity scores for each of the pixels of the first and second images, respectively. For example, the object region in the first image segmentation results can be used as a template (e.g., a 3D template). After calculating the respective neutrosophic similarity scores for each of the pixels of the second image (e.g., step 212), a rotation on the template (e.g., the 3D template) can be taken and the neutrosophic score difference of the object region of the second image can be computed, which is shown in Eqn. (14).

$$Dif_{NS}(x_0, y_0, z_0, \phi) = \sum_{x=1}^{H} \sum_{y=1}^{W} \sum_{z=1}^{L} |NS_2(x+x_0, y+y_0, z+z_0) - NS_t(x, y, z)| \quad (14)$$

where $NS_1$ is the respective neutrosophic similarity scores for each of the pixels of the first image, $NS_2$ is the respective neutrosophic similarity scores for each of the pixels of the second image, and x, y and z are pixel coordinates in 3D space. A loop can then be taken on $x_0$, $y_0$, $z_0$ and $\varphi$ in the range of $[1\ H_2]$, $[1\ W_2]$, $[1\ Z_2]$ and $[-10\ 10]$, respectively, where $H_2$, $W_2$ and $Z_2$ are the height, width and length of the second image. The optimal $x_0$, $y_0$, $z_0$ and $\varphi$ can be obtained with the lowest $Dif_{NS}$. Then, at 216, the first and second images can be registered using the one or more registration parameters. For example, the template (e.g., the 3D template) can be transformed using the optimal $x_0$, $y_0$, $z_0$ and $\varphi$ as the registration parameters, and the transformed result can be used as the object region within the second image.

Optionally, in order to refine the object region of the second image as determined through the registration algorithm described above, the object in the second image can be segmented from background using the region growing algorithm described above with regard to FIG. 1. Optionally, this segmentation can include receiving a margin adjustment related to the object segmented from the background of the second image. The margin adjustment is an adjustment to the margins or boundaries around the object segmented from the background of the second image. For example, a medical professional (e.g., a radiologist) can review the segmented image, and based on his knowledge and experience, manually refine (e.g., expand or contract) the margins or boundaries of the object segmented using the region growing algorithm.

Alternatively or additionally, after segmenting the first image (e.g., the pre-operative image) using the region growing algorithm at step 206, an annotation related to the object segmented from the background of the first image can be received. For example, a medical professional (e.g., a radiologist) can analyze the segmented image and/or the object and provide the annotation (measurements, labels, notes, etc.) in order to highlight features (e.g., suspicious areas, blood vessels, vital structures, surrounding organs, etc.) contained within the first image and/or the object. It should be understood that the annotations can be used by another medical professional such as a surgeon, for example, as guidance during a subsequent medical procedure or consultation. The annotation related to the object segmented from the background of the first image can be stored, for example, for subsequent use by overlaying and displaying the annotation relative to the second image (e.g., the real-time, intra-operative image). This disclosure contemplates that the segmented object and/or the annotation can be displayed in a 2D or 3D rendering with or without performing the margin adjustment. Optionally, the segmented object and/or the annotation can be displayed using an AR head-mounted device (described below).

Figure 3:
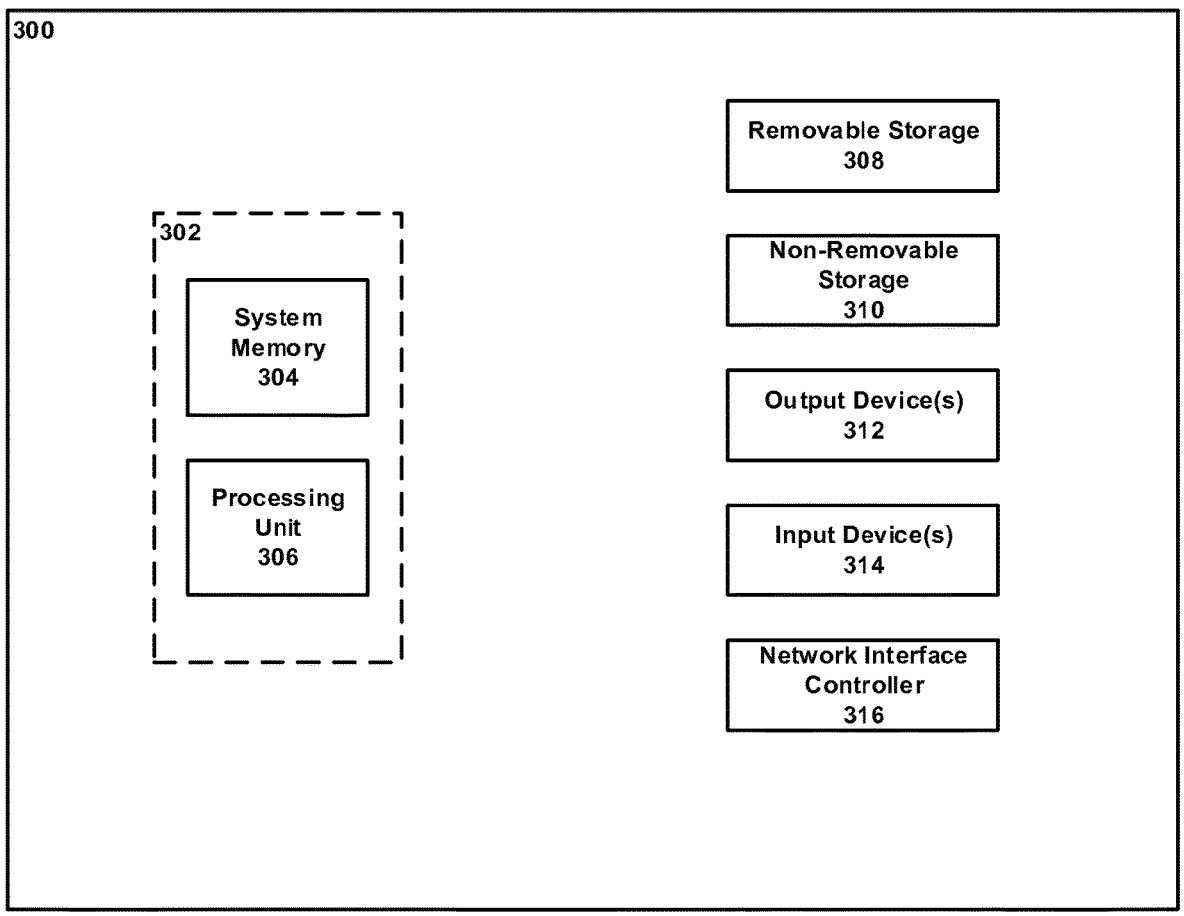
FIG. 3 is a block diagram of an example computing device.

When the logical operations described herein are implemented in software, the process may execute on any type of computing architecture or platform. For example, referring to FIG. 3, an example computing device upon which embodiments of the invention may be implemented is illustrated. In particular, at least one processing device described above may be a computing device, such as computing device 300 shown in FIG. 3. The computing device 300 may include a bus or other communication mechanism for communicating information among various components of the computing device 300. In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor that performs arithmetic and logic operations necessary for operation of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Computer-readable media refers to any media that is capable of providing data that causes the computing device 300 (i.e., a machine) to operate in a particular fashion. Various computer-readable media may be utilized to provide instructions to the processing unit 306 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

Computing device 300 typically includes a variety of computer-readable media. Computer-readable media can be any available media that can be accessed by device 300 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 304, removable storage 308, and non-removable storage 310 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 300. Any such computer storage media may be part of computing device 300.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Figure 4:
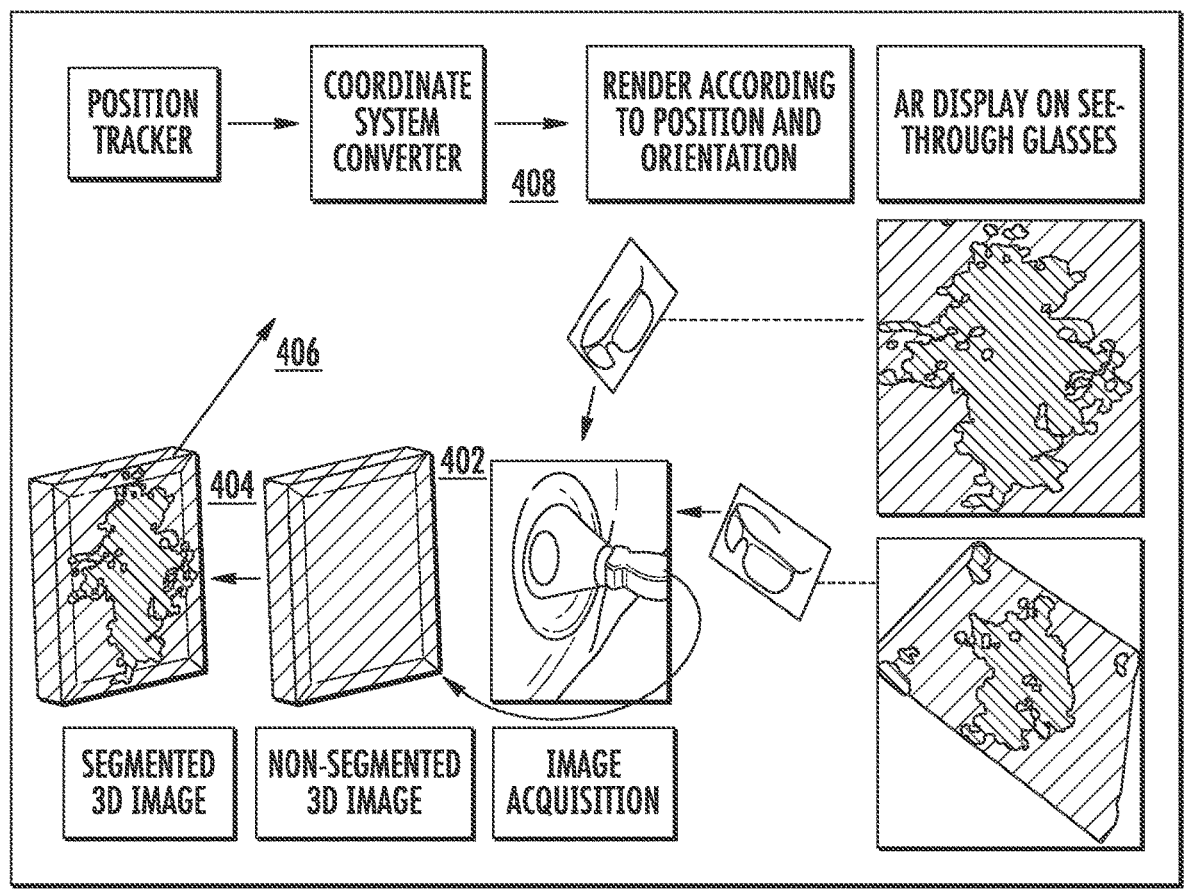
FIG. 4 is a flow diagram of example operations for providing real-time visualization of a prior image analysis on real-time images.

FIG. 4 is a flow diagram of example operations for providing real-time visualization of a prior image analysis on real-time images. The example operations were used to evaluate 3D ultrasound images and confirm accuracy for real-time volumetric analysis. The example operations include performing the segmentation and registration algorithms described with regard to FIGS. 1 and 2. For example, at 402, a pre-operative image is acquired. The pre-operative image provides a 3D visualization of an object (e.g., a tumor within breast tissue). As described above, the tumor can be segmented from the background of the pre-operative image using the region growing algorithm based on neutrosophic similarity scores. A medical professional (e.g., a radiologist) then marks suspicious areas for later resection, i.e., the radiologist provides the annotations described above. Thereafter, a real-time, intra-operative ultrasound image is acquired, for example, using the iU22 xMATRIX ULTRASOUND SYSTEM from KONINKLIJKE PHILIPS N.V. of EINDHOVEN, THE NETHERLANDS. The real-time, intra-operative ultrasound image provides a 3D visualization of the tumor within breast tissue. As described above, the pre-operative image and the real-time, intra-operative ultrasound image are registered using a registration algorithm based on neutrosophic similarity scores. By registering the pre-operative image and the real-time, intra-operative ultrasound image, the annotation made to the pre-operative image (e.g., the prior analysis) can be imported and overlaid on (or fused with) the real-time, intra-operative image, which is shown at 404. This allows for real-time visualization of the tumor with the radiologist's annotation. The precision of the image segmentation and registration algorithms described herein are confirmed in by the feasibility study results of Table 1, showing an accuracy of less than 1.5 mm deviation per axis. These results demonstrate the accuracy and reliability of real-time, 3D visualization.

TABLE 1

| Accuracy of Algorithms (n = 27) | | | |
|---|---|---|---|
| Axis | x (mm) | y (mm) | z (mm) |
| Accuracy | 1.44 | 1.61 | 0.85 |
| SD | 1.66 | 1.50 | 0.89 |
| SEM | 0.43 | 0.39 | 0.23 |

Figure 4A:
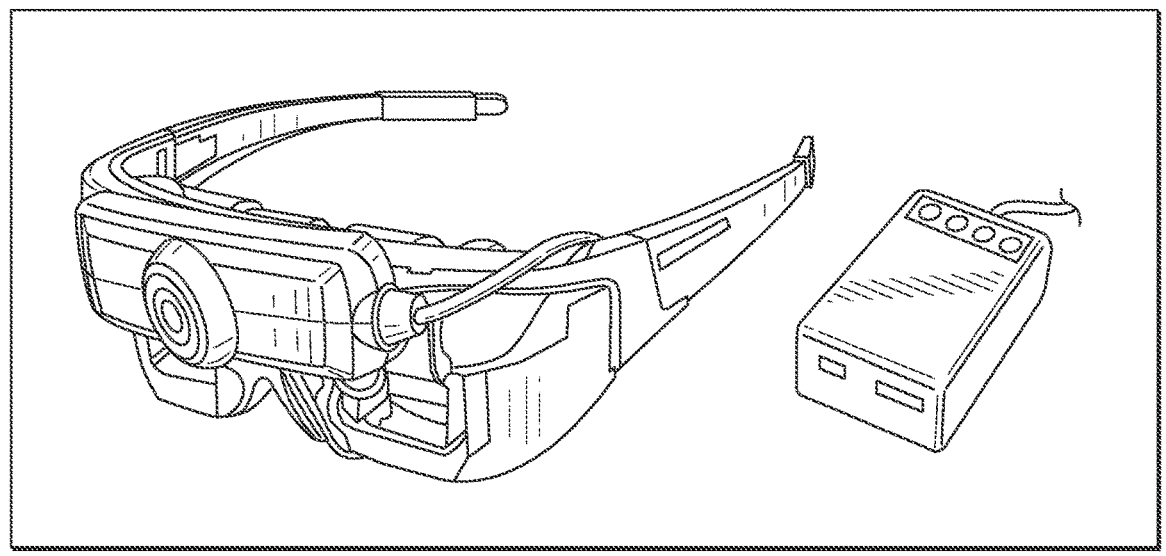
FIG. 4A is an example AR head-mounted device used in the example operations shown in FIG. 4.

The enhanced images (e.g., the real-time, intra-operative ultrasound image with annotations overlaid) can be displayed, and optionally, in a 3D modality. For example, the image segmentation and registration algorithms described above can be integrated with head-tracking (HT) and AR technologies (e.g., the "AR head-mounted device" as used herein). One example AR head-mounted device is the VUZIX STAR 1200XLD from VUZIX CORPORATION of ROCHESTER, NEW YORK, which is shown in FIG. 4A. Although the VUZIX STAR 1200XLD is provided as an example, this disclosure contemplates integrating the image segmentation and registration algorithms with other AR head-mounted devices. Alternatively or additionally, this disclosure contemplates displaying the real-time, intra-operative ultrasound image with the overlaid annotation on a handheld device such as a handheld device running the WINDOWS, ANDROID or IOS operating systems. This can provide surgeons with an accurate, real-time, 3D navigation tool for intra-operative guidance, facilitating complete tumor excision. For example, at 406, the real-time, intra-operative ultrasound image with the overlaid annotation can be transmitted to the AR head-mounted device. The computing device that performs the image segmentation and/or registration algorithms can be communicatively connected with the AR head-mounted device through a communication link. This disclosure contemplates the communication link is any suitable communication link. For example, a communication link may be implemented by any medium that facilitates data exchange between the network elements including, but not limited to, wired, wireless and optical links. The real-time, intra-operative ultrasound image with the overlaid annotation can then be displayed on the AR head-mounted device.

The AR head-mounted device can optionally be configured to implement optical tracking technology, for example, to track a surgeon's eye movements. Eye movements can include, but are not limited to, movement of the surgeon's pupil(s) and/or blinking. Using optical tracking technology, various functionality (e.g., zoom functions, illumination functions, etc.) of the AR head-mounted device can be controlled based on the surgeon's eye movements. For example, a specific blinking pattern can activate the zoom functionality of the AR head-mounted device in order to increase/decrease the amount of zoom on the real-time, intra-operative ultrasound image. Alternatively or additionally, specific pupil movement can pan the real-time, intra-operative ultrasound image. It should be understood that the movements and functionalities described above are only provided as examples and should not be limiting. This disclosure contemplates that various functionalities can be controlled using various eye movements.

Alternatively or additionally, the AR head-mounted device can optionally be configured to implement optical character recognition technology. The AR head-mounted device can be configured to recognize text and/or display information related to the text on the display. For example, the AR head-mounted display can be configured to recognize text on a medicinal container (e.g., a drug name) and can display related information such as dosage, side effects, etc. on a portion or quadrant of the display. The AR head-mounted device can optionally retrieve the related information from a network over the communication link discussed above. This disclosure contemplates that the information related to the text can be displayed on a portion (e.g., an upper quadrant) of the display area, while the real-time, intra-operative ultrasound image is simultaneously displayed in another portion (e.g., a central portion) of the display area.

The HT technology of the AR head-mounted device allows the computing device that performs the image segmentation and/or registration algorithms to detect the position and orientation of a user's (e.g., the surgeon's) head to display the image as an AR figure. For example, at 408, information regarding a user's movement can be received at the computing device from the AR head-mounted device, and the computing device can adjust a position and/or an orientation of the real-time, intra-operative ultrasound image with the overlaid annotation. The adjusted real-time, intra-operative ultrasound image with the overlaid annotation can then be transmitted to the AR head-mounted device by the computing device, for example, for display on the AR head-mounted device. Accordingly, in addition to the potential "x-ray vision" (e.g., seeing the tumor underneath the skin) capability, the AR head-mounted device has a see-through display, allowing the surgeon to operate simultaneously in a traditional manner.

Referring now to FIG. 5, tables showing the results of a feasibility study are shown. A total of sixty six images were evaluated (i.e., three images from human subjects and sixty three images from breast phantoms). Thirty two images (including the three images from human subjects) were analyzed for single tumor detection and thirty four images were analyzed for multi-tumor detection. The accuracy between a radiological volume-of-resection (rVOR or pre-operative image) and a real-time surgical volume-of-resection (sVOR or real-time intraoperative image) was calculated. Single tumors ranged from 1.3 to 10.47 $cm^3$ in volume, and eighteen tumors had hypodense features on US. Referring to Table 1 in FIG. 5, comparison of the sVOR was within 1.5 mm from the rVOR per axis, providing a volumetric accuracy of 1.1 $mm^3$ (range: 0.02-12.2 $mm^3$; SD: 1.8 $mm^3$; SEM: 0.04 $mm^3$). Multi-tumor visualization had similar results, and twenty one of tumors had hypodense features on US. Between each tumor, there were 2.2 to 5.3 mm in distance, thirty images contained two tumors, and four images had three tumors to be visualized. All tumors were all recognized as independent tumors on intraoperative visualization, and the sVOR was within 2.5 mm of the preoperatively analyzed rVOR per axis. Referring to Table 2 in FIG. 5, this gives a volumetric accuracy of 5.4 mm3 (range 1.3-8.5 $mm^3$; SD 2.6 $mm^3$; SEM 0.08 $mm^3$).

Computer Assisted Surgery (CAS)

A CAS system using 3D breast ultrasound (BUS) images is described below. The CAS system can segment and visualize the breast cancer for assisting surgeons during operations. Due to the large variations in pathology that may be present in BUS images, it can be difficult to extract the tumor regions accurately, especially when the breast has a great number of distortions during the operation. Techniques that can provide accurate tumor segmentation and visualization, including those affected by distortion problem, are provided below.

A CAS system is described that uses a tumor segmentation technique based on template matching and region growing algorithms on BUS images to improve the tumor segmentation accuracy. A template matching (TM) algorithm can be employed to identify the sub volume of interest (VOI) enclosing the tumor in the BUS image captured in real time during the operation (e.g., the intra-operative image). The VOI is also referred to herein as a region of interest (ROI). The referenced template can be obtained from a different BUS image captured previous to the operation (e.g., the pre-operative image), and the tumor in the pre-operative image can be identified by a medical professional such as a radiologist manually. Then, a region growing algorithm can optionally be used to segment the tumor region in the sub VOI. The initial seed region and growing strategy can be determined by the characteristics of the VOI. Finally, the detected tumor can be visualized using 3D rendering algorithm such that it is displayed for surgeons in real time using portable digital glasses (e.g., an AR head-mounted device), for example.

One challenging task for a breast cancer CAS system is to identify the exact position of the ROI enclosing the tumors. The complexity relies on the difference in angulation and placement of the transducer while obtaining the BUS images during operation. This often alters the boundaries of the images and in some cases the new image may even miss important areas of the region of interest.

To address this challenge, a tumor segmentation algorithm based on template matching and region growing algorithms on 3D BUS images can be used. For example, a 3D BUS image can be captured before surgery (e.g., a pre-operative image) and can be manually segmented with the tumors' approximate boundaries outlined by a medical professional. This image is also referred to herein as the primary image or template image. After this information is saved for the particular BUS image, a template matching (TM) algorithm can be employed to identify the volume of interest of the subsequent (e.g., secondary) 3D BUS images, which can optionally be captured in real time during surgery (e.g., intra-operative images). These images are also referred to herein as secondary images. The manual breast tumor segmentation performed over the primary image can be treated as a reference for the template matching algorithm, and an initial region for the next refinery segmentation algorithm. A region growing (RG) algorithm can then optionally be used to refine the tumor region using the result after template matching algorithm. The detected tumor can be visualized using 3D rendering algorithm and displayed for surgeons in real time, for example, using portable digital glasses (e.g., an AR head-mounted device).

Figure 6:
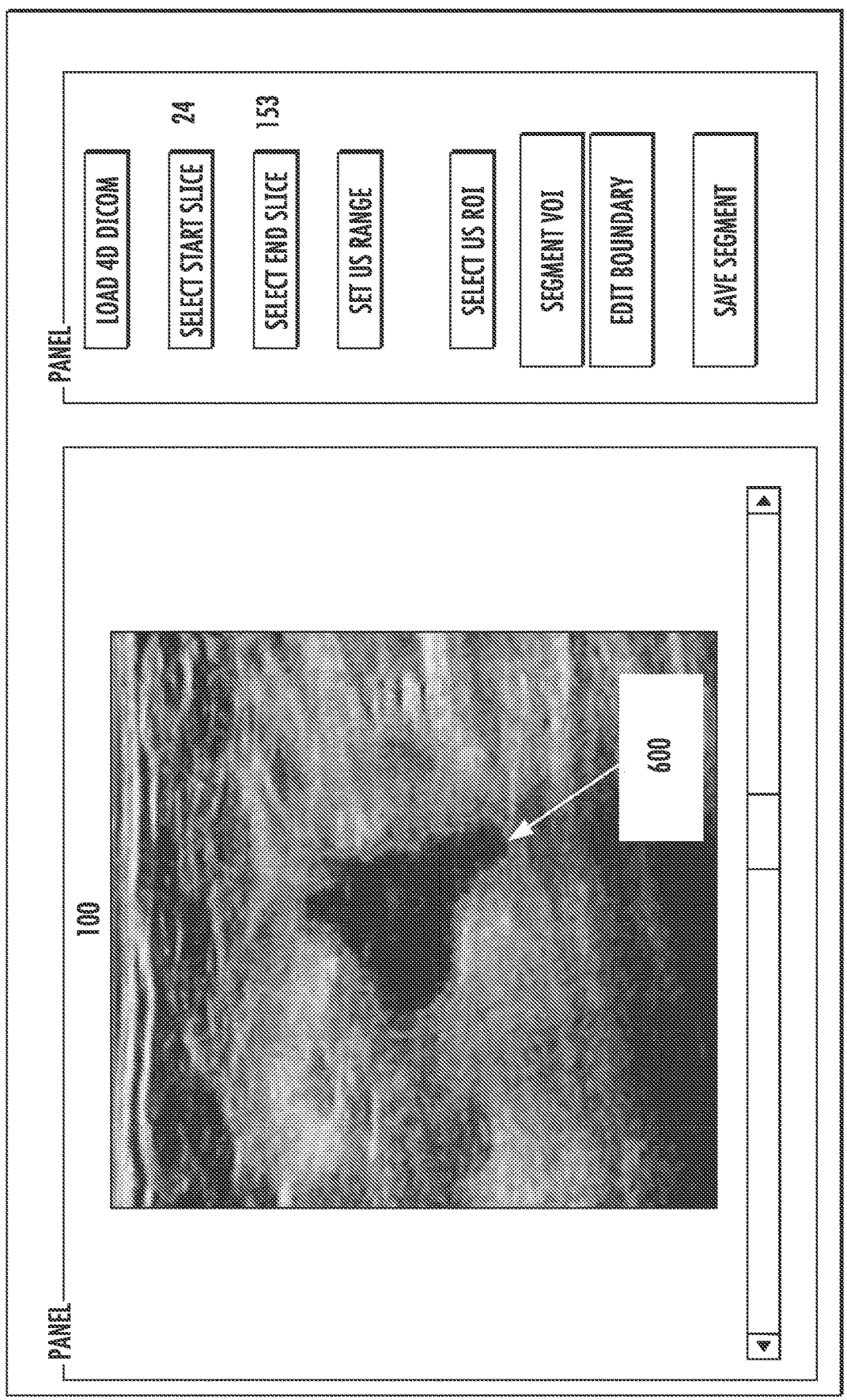
FIG. 6 shows an example of a radiologist's outline on a single image slice.

An interactive segmentation algorithm can be employed to allow the user to place markings and other relevant information to be used during a subsequent surgical procedure. For example, a radiologist can manually outline the tumor boundaries on the transverse views (e.g., slices) using a graphic user interface (GUI) program. FIG. 6 shows an example of a radiologist's outline 600 (or manual segmentation) on a single image slice. A radiologist can outline the area to be resected, for example. This information will be saved and displayed during a surgical procedure to guide the surgeons appropriately. A template matching (TM) algorithm can be employed to identify the initial tumor region in the 3D BUS image(s) (e.g., the secondary images) captured during operation. The tumor volume developed in the template image ($V_1$) is defined as a template denoted as $V_{TM}$. Then, a template matching algorithm can be used to find the initial tumor region over the secondary images, which are optionally taken during the surgical procedure. In the TM method, a local window volume $V_{CW}$ with the same size as $V_{TM}$ is moved onto the intra-operative or secondary image, and denoted as $V_2$ to find the local sub volume that better correlate $V_{TM}$. The similarity can be defined by matching the differences between the $V_{CW}$ and $V_{TM}$.

Furthermore, $V_2$ can have some rotations and variations compared to $V_1$. To find the optimal matching, the volume template $V_{TM}$ can be rotated in several angles over the axis perpendicular to the breast and chest planes, and the similarity can be computed as the intensity difference between the $V_{CW}$ and the rotated template $V_{TM}^{\emptyset}$. The difference between the $V_{CW}$ and $V_{TW}^{\emptyset}$ can be defined as:

$$D(x_0, y_0, z_0, \emptyset_0) = \Sigma_{x=1}^{HTM} \Sigma_{y=1}^{WTM} \Sigma_{z=1}^{LTM} |V_{CW}(x+x_0, x+x_0, x+x_0) - V_{TW}^{\emptyset_0}(x, y, z)|$$

where $x_0$, $y_0$ and $z_0$ are the starting coordinate of the current window volume in the second image. $V_{TW}^{\emptyset_0}$ is the rotated template volume with angle $\emptyset_0$. $H_{TM}$, $W_{TM}$ and $L_{TM}$ are the height, width and length of the $V_{TM}$, respectively. The local window volume $V_{CW}^*(x_0^*, y_0^*, z_0^*, \emptyset^*)$ with the lowest difference can be treated as the VOI with the tumor candidate:

$$V_{CW}^*(x_0^*, y_0^*, z_0^*, \emptyset^*) = \underset{0 \le x_0 \le H_2, 0 \le y_0 \le W_2, 0 \le z_0 \le L_2, \emptyset_{min} \le \emptyset \le \emptyset_{max}}{\mathrm{argmin}} (D(x_0, y_0, z_0, \emptyset_0))$$

The steps of the initial tumor region identification can be summarized as follows. First, the manual segmentation result in the first BUS image $V_1$ (e.g., the pre-operative image) can be used as a volume template $V_{TM}$. Then, a rotation on the $V_{TM}$ around the axis perpendicular to the breast and chest plane can be taken, and the difference of the rotated volume template $V_{TW}^{\emptyset}$ and a local window volume $V_{CW}$ in the second BUS image (e.g., the intra-operative image) can be computed. Loops on $x_0$, $y_0$, $z_0$ and $\phi$ in the range of $[1\ H_2]$, $[1\ W_2]$, $[1\ L_2]$ and $[\phi_{min}, \phi_{max}]$, respectively, can be taken, where $H_2$, $W_2$ and $L_2$ are the height, width and length of the second BUS image, respectively. Then, the optimal local window volume $V_{CW}^*$ with the lowest difference value D as the sub volume enclosing tumor region in the intra-operative image can be obtained. The tumor result in the first BUS image can be rotated using the optimal angle $\phi^*$, and shift it according to the distance between the point $(x_0^*, y_0^*, z_0^*)$ and the point $(x_0, y_0, z_0)$. The rotated and shifted tumor region can be denoted as $V_m^*$.

After the template matching algorithm, the reference segmentation tumor region in the first BUS image (e.g., the pre-operative image) is mapped onto the secondary BUS image (e.g., the intra-operative image) in operation by being rotated around the axis perpendicular to the chest plane using the optimal angle $\phi^*$, and shifted according to the distance between the point $(x_0^*, y_0^*, z_0^*)$ and the point $(x_0, y_0, z_0)$. Using the rotated and shifted tumor region $V_m^*$ as the initial region, a region growing algorithm can optionally be used to obtain the refined tumor segmentation according to the characteristic in the second BUS image.

A region growing is a frequently used segmentation technique. This is a kind of region-based image segmentation technique. To make the segmentation completely automatic, most of the region growing methods incorporate automatic selection of the initial seed regions. This approach examines neighboring pixels of initial "seed points" and determines whether the pixel neighbors should be added to the region. Therefore, there are two parameters for the region growing algorithm: (i) seed points and (ii) criterion to add the neighbor pixels into the region. The region growing algorithm integrates the neighbor pixels iteratively into the tumor region which are similar to the pixel in $V_m^*$. The growing and stopping criterion are determined automatically according to the characteristics of the reference region after transformation.

The seed point region $V^{(0)}$ can be selected using the pixels in the reference region after transformation, and the criterion can be determined based on the intensity difference between the neighbor pixels and the mean value of the current seed point region as follows:

$$V^{(0)} = V_{CW}*$$

$$V^{(t)} = \{p \mid abs(I_p - \bar{I}_{V^{(t-1)}}) \leq I_{th}\},$$

where abs() is the absolution function. p is a pixel in the neighborhood and $I_p$ is the intensity of the pixel p. $\bar{I}_{V^{(t-1)}}$ is the average intensity value of the region $V^{(t-1)}$. The procedure can be taken iteratively until no pixel satisfies the criterion.

Figure 7:
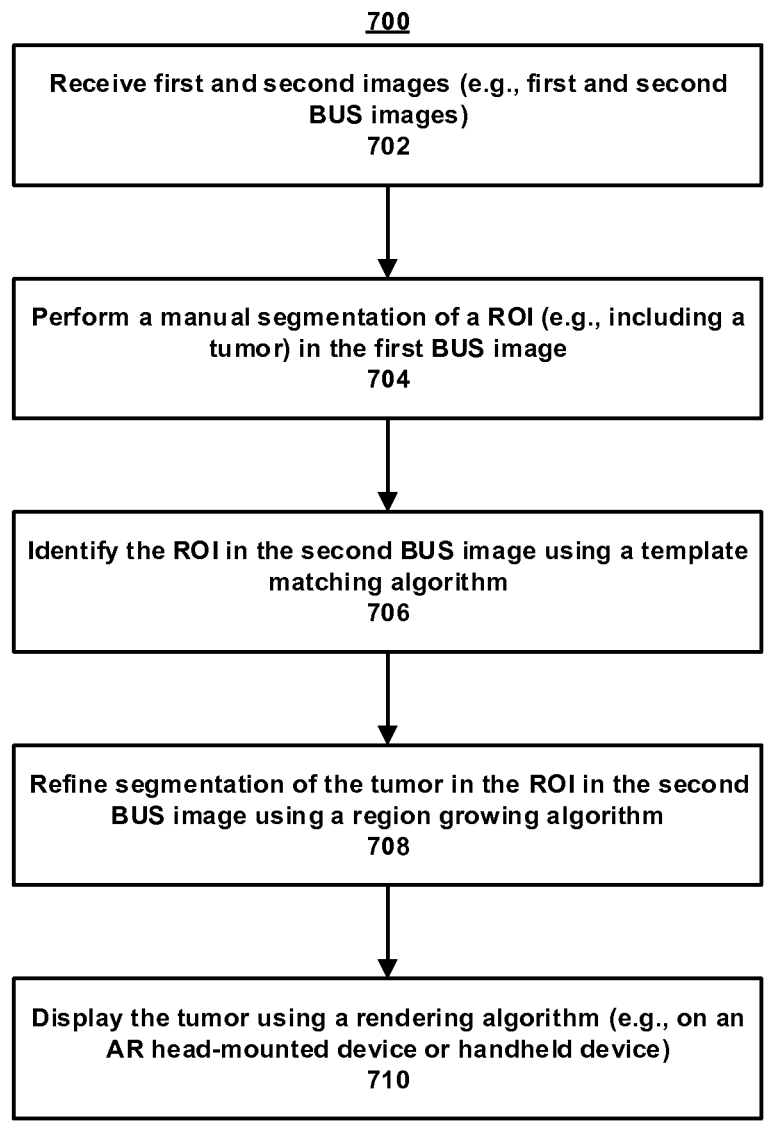
FIG. 7 is a flow diagram illustrating example operations for segmenting and visualizing (e.g., displaying) tumors for use during surgical procedure.

Referring now to FIG. 7, example operations 700 for segmenting and visualizing (e.g., displaying) tumors for use during surgical procedure are described. At 702, a plurality of images are received. The images can be 3D BUS images, for example. This disclosure contemplates that the images can be images taken using imaging modalities other than 3D ultrasound. Additionally, one of the images can be a template image. The template image can be a first 3D BUS image, for example, an image taken before a surgical procedure (e.g., a pre-operative image). The other image can be a second 3D BUS image, for example, an image taken in real time during the surgical procedure (e.g., an intra-operative image). At 704, a region of interest (ROI) in the first 3D bus image can be manually segmented, for example, by a radiologist or other medical professional. For example, the radiologist can optionally outline an area to be resected (e.g., a tumor). In other words, the ROI can include the tumor. At 706, using the first 3D BUS image as a template image, a template matching (TM) algorithm can be used to identify the ROI in the second BUS image. In this step, for example, the ROI includes the tumor to be extracted during the surgical procedure. Then, at 708, segmentation of the tumor can optionally be refined using a region growing (RG) algorithm. Then, at 710, the tumor can be visualized using 3D rendering algorithm such that it is displayed for surgeons in real time, for example, using portable digital glasses (e.g., an AR head-mounted device) or a handheld device.

Using the above techniques, the tumor boundaries manually outlined by a radiologist on the transverse views can be used as the reference standard for the performance evaluation of the automated tumor segmentation algorithm. Linear interpolation can be performed to fill the gaps between the manually drawn sparse boundary points. Let $C=\{c_1, c_2, \ldots, c_p\}$ be the computer-identified tumor boundary that contains p singly-connected points, and $R=\{r_1, r_2, \ldots, r_q\}$ be radiologist's manually outlined and filled tumor boundary that contains q singly-connected points. The Euclidean distance between a computer-identified tumor boundary point $c_i$ and a reference standard point $r_j$ is $Dist(c_i, r_j)$, or equivalently, $Dist(r_j, c_i)$. For each transverse view on which the radiologist manually outlined the tumor boundaries, the accuracy of tumor boundary detection is evaluated by three performance metrics described below.

(1) Percent overlap area (POA):

$$POA(C, R) = \frac{A_C \cap A_R}{A_C \cup A_R}$$

where $A_C$ and $A_R$ are the computer segmented tumor area and the reference standard tumor area enclosed by the boundaries C and R. $\cup$ and $\cap$ are the union and intersection of two sets, respectively.

(2) Hausdorff distance between the boundaries C and R (Hdist):

$$Hdist = \max\{\max_{c_i \in C}\{\min_{r_j \in R}\{Dist(c_i, r_j)\}\}, \max_{r_j \in R}\{\min_{c_i \in C}\{Dist(r_j, c_i)\}\}\}$$

(3) Average distance between the boundaries C and R (AvgDist):

$$AvgDist = \frac{1}{2}\left(\frac{1}{p}\sum_{i=1}^{p}\min_{r_j \in R}\{Dist(c_i, r_j)\} + \frac{1}{q}\sum_{j=1}^{q}\min_{c_i \in C}\{Dist(r_j, c_i)\}\right)$$

The distance measures are calculated in units of mm.

Figure 8:
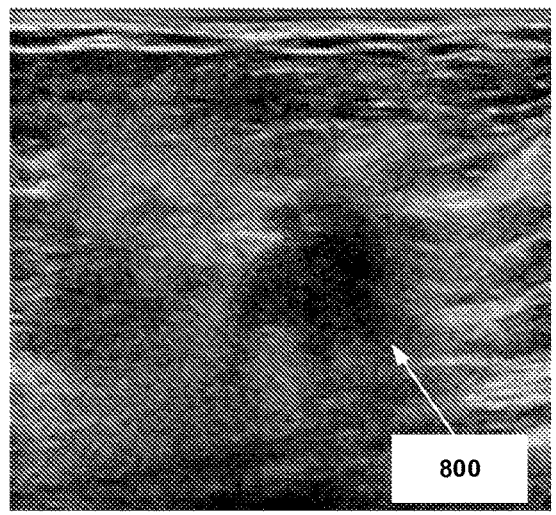
FIGS. 8A-8C show three examples of the segmented tumor regions using the segmenting techniques described in FIG. 7.
Figure 8:
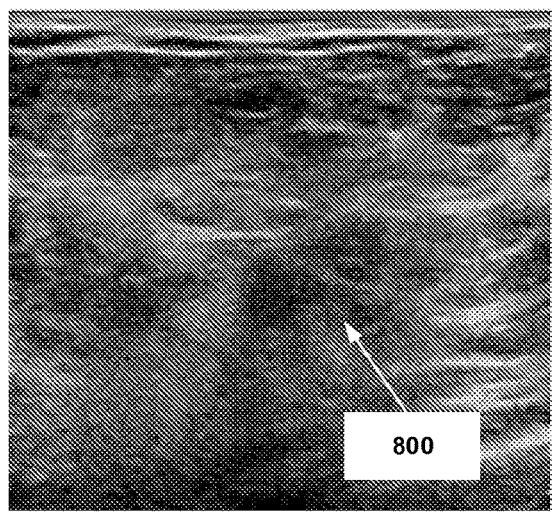
Figure 8:
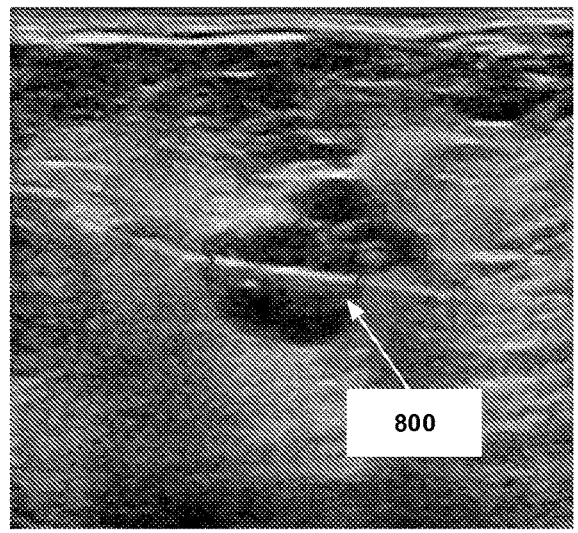

FIGS. 8A-C show three examples of the segmented tumor regions using the technique described above. FIG. 8A shows a case with a solid tumor. FIG. 8B shows a case having nonsolid tumor. FIG. 8C shows a case with a wire inside the tumor. The boundaries of segmentation results are marked using lines 800.

In an example test with 15 test phantom cases, the tumor boundaries were outlined on a total of 31435 slices, which were used as the reference standard for performance evaluation. In comparison with radiologist's manual outlines, the performance metrics (POA, Hdist and AvgDist) were calculated on the corresponding slices and the mean and standard deviation were computed over the 31435 slices. As shown in Table 2 below, the mean and standard deviation of the POA, Hdist and AvgDist were improved from 81.4±5.2%, 34.8±3.2 mm, and 3.3±3.1 mm using the segmentation technique described with reference to FIG. 7 without the region growing algorithm (e.g., skipping step 708) to 889.4±5.6%, 7.9±8.4 mm, and 0.9±1.1 mm using the region growing algorithm (e.g., performing step 708), respectively. The improvement is statistically significant (p<0.05) for each performance metric by t-test.

Table 2 below show the performance of computer segmentation using the segmentation technique described with reference to FIG. 7 without the region growing algorithm (e.g., skipping step 708) (RG in Table 2) and using region growing algorithm (e.g., performing step 708) (NRG in Table 2). The P-values of the differences between the two methods are estimated by the t-test.

| Method  | POA (%)    | Hdist (mm)  | AvgDist (mm) |
|---------|------------|-------------|--------------|
| NRG     | 81.4 ± 5.2 | 34.8 ± 3.2  | 3.3 ± 3.1    |
| RG      | 89.4 ± 5.6 | 7.9 ± 8.4   | 0.9 ± 1.1    |
| P-value | $<10^{-3}$ | $<10^{-4}$  | $<10^{-5}$   |

Figure 9:
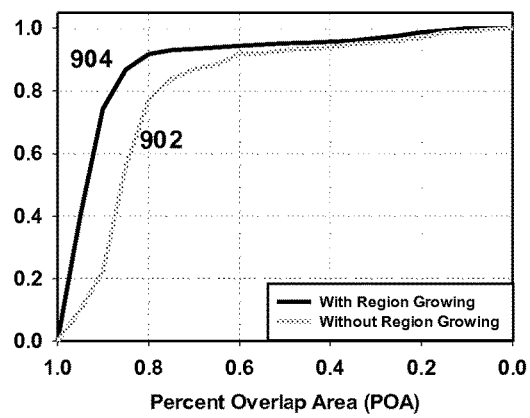
FIGS. 9A-9C show the cumulative percentage of slices relative to the 31435 slices with phantom tumor regions as reference standards in an example test.
Figure 9:
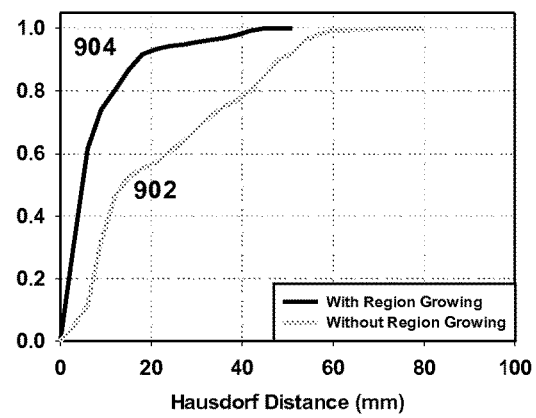
Figure 9:
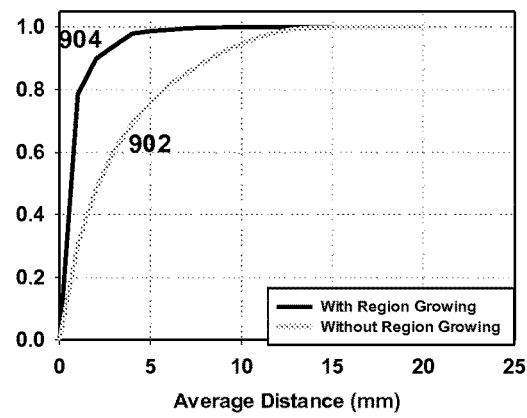

FIGS. 9A-9C show the cumulative percentage of slices relative to the 31435 slices with phantom tumor regions as reference standards in an example test. For example, FIGS. 9A-9C show the cumulative percentage of slices having POV and POA greater than a certain value and Hdist and AvgDist smaller than a certain value, respectively. In FIGS. 9A-9C, the results of the segmentation technique described with reference to FIG. 7 without the region growing algorithm (e.g., skipping step 708) are shown by line 902 and using the region growing algorithm (e.g., performing step 708) are shown by line 904. FIG. 9A shows the percent overlap area (POA) between the tumor region segmented using the technique described above and the reference standard greater than a certain value. FIG. 9B shows the Hausdorff distance measurement. FIG. 9C shows the average Euclidean distance measurement between the segmented boundary and the reference standard smaller than a certain value. These figures shows that 93.5% (29391/31435) of slices in the computer-segmented tumors had POA 85%, and that 80% (25148/31435) and 98.8% (31057/31435) of slices in the computer-segmented tumor boundaries had Hdist ≤12 mm, and AvgDist ≤5 mm, respectively.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for registering a plurality of images containing an object, comprising:
    receiving, using at least one processor, a first image including a plurality of pixels;
    calculating, using the at least one processor, respective first neutrosophic similarity scores for each of the pixels of the first image;
    segmenting, using the at least one processor, an object from background of the first image using a region growing algorithm based on the respective first neutrosophic similarity scores for each of the pixels;
    receiving, using the at least one processor, a margin adjustment related to the object segmented from the background of the first image;
    receiving, using the at least one processor, a second image including a plurality of pixels;
    calculating, using the at least one processor, respective second neutrosophic similarity scores for each of the pixels of the second image;
    performing, using the at least one processor, a template matching algorithm based on differences between the respective first and second neutrosophic similarity scores for each of the pixels of the first and second images, respectively, to determine one or more registration parameters; and
    registering, using the at least one processor, the first and second images using the one or more registration parameters, wherein the respective first and second neutrosophic similarity scores for each of the pixels of the first and second images, respectively, are calculated using a respective neutrosophic set domain for each of a plurality of pixel characteristics, wherein the respective neutrosophic set domains comprise a neutrosophic set domain for intensity values and a neutrosophic set domain for homogeneity values, and wherein each of the respective neutrosophic set domains includes a true value, an indeterminate value, and a false value.

2. The method of claim 1, wherein the one or more registration parameters are determined by minimizing the differences between the respective first and second neutrosophic similarity scores for each of the pixels of the first and second images, respectively.

3. The method of claim 1, further comprising segmenting, using the at least one processor, the object from background in the second image using the region growing algorithm based on the respective second neutrosophic similarity scores for each of the pixels.

4. The method of claim 3, further comprising receiving, using the at least one processor, a margin adjustment related to the object segmented from the background of the second image.

5. The method of claim 3, wherein a pixel is merged into a region containing the object under the condition that the respective first or second neutrosophic similarity score for the pixel is less than a threshold value.

6. The method of claim 3, wherein a pixel is merged into a region containing the background under the condition that the respective first or second neutrosophic similarity score for the pixel is greater than a threshold value.

7. The method of claim 1, wherein calculating the respective first or second neutrosophic similarity scores for each of the pixels of the first or second image further comprises:
    transforming, using the at least one processor, a plurality of pixel characteristics of the first or second image into respective neutrosophic set domains; and
    calculating the respective first or second neutrosophic similarity scores for each of the pixels based on the respective neutrosophic set domains for the pixel characteristics.

8. The method of claim 7, wherein the plurality of pixel characteristics include a respective intensity, a respective textural value and a respective homogeneity of each of the pixels.

9. The method of claim 8, wherein calculating the respective first or second neutrosophic similarity scores for each of the pixels based on the respective neutrosophic set domains for the pixel characteristics further comprises:
    calculating respective first or second neutrosophic similarity scores for each of the respective neutrosophic set domains; and
    calculating a mean of the respective first or second neutrosophic similarity scores for each of the respective neutrosophic set domains.

10. The method of claim 8, wherein the respective intensity of each of the pixels is transformed into the neutrosophic set domain for intensity values based on the respective intensity value.

11. The method of claim 8, wherein the respective homogeneity of each of the pixels is transformed into the neutrosophic set domain for homogeneity values based on the respective homogeneity value.

12. The method of claim 11, further comprising filtering the first or second image to obtain the respective homogeneity of the pixel.

13. The method of claim 1, further comprising:
    transmitting, using the at least one processor, the second image to an augmented reality ("AR") head-mounted device; and
    displaying, using the AR head-mounted device, the second image.

14. The method of claim 13, further comprising:
    receiving, using the at least one processor, information regarding a user's movement from the AR head-mounted device;
    adjusting, using the at least one processor, at least one of a position or an orientation of the second image; and
    transmitting, using the at least one processor, the adjusted second image to the AR head-mounted device.

15. The method of claim 13, further comprising:
- receiving, using the at least one processor, an annotation related to the object segmented from the background of the first image;
- storing, using the at least one processor, the annotation related to the object segmented from the background of the first image;
- overlaying the annotation relative to the object segmented from the background of the second image; and
- displaying, using the AR head-mounted device, the second image with the overlaid annotation.

16. The method of claim 1, wherein the first image is a pre-operative image and the second image is a real-time, intra-operative image.

17. The method of claim 1, wherein each of the first and second images provides a 2D or 3D visualization of the object.

18. method of claim 1, wherein the object includes a lesion region of interest.

19. The method of claim 1, wherein the at least one processor is part of a cloud computing environment.

* * * * *